United States Patent [19]

Sivam et al.

[11] Patent Number: 5,521,290
[45] Date of Patent: May 28, 1996

[54] TARGETING SUBSTANCE-DIAGNOSTIC/THERAPEUTIC AGENT CONJUGATES HAVING SCHIFF BASE LINKAGES AND METHODS FOR THEIR PREPARATION

[75] Inventors: Gowsala P. Sivam, Edmonds; A. Charles Morgan, Jr.; Vivekananda M. Vrudhula, both of Edmonds, all of Wash.

[73] Assignee: NeoRx Corporation, Seattle, Wash.

[21] Appl. No.: 342,789

[22] Filed: Nov. 21, 1994

Related U.S. Application Data

[62] Division of Ser. No. 987,535, Dec. 7, 1992, abandoned, which is a continuation of Ser. No. 714,806, Jun. 13, 1991, abandoned, which is a division of Ser. No. 415,154, Sep. 29, 1989, Pat. No. 5,066,789, which is a continuation-in-part of Ser. No. 252,298, Sep. 30, 1988, abandoned.

[51] Int. Cl.$^6$ .......................... C07K 16/00; C07K 16/46; C07K 19/00
[52] U.S. Cl. .................... 530/391.5; 530/391.9; 530/402; 530/409
[58] Field of Search ............... 530/391.9, 391.5, 530/402, 409

[56] References Cited

U.S. PATENT DOCUMENTS

| | | | |
|---|---|---|---|
| 3,959,080 | 5/1976 | Orth et al. ........................ | 530/395 |
| 4,093,607 | 6/1978 | Sela et al. ........................ | 530/388 |
| 4,153,417 | 5/1979 | Hällgren et al. .................. | 23/230 B |
| 4,314,987 | 2/1982 | Morris et al. ..................... | 424/1 |
| 4,443,426 | 4/1984 | Thakur ............................. | 424/1.1 |
| 4,634,586 | 1/1987 | Goodwin et al. .................. | 424/1.1 |
| 4,671,958 | 6/1987 | Rodwell et al. . | |
| 4,735,792 | 4/1988 | Srivastava ......................... | 424/1.1 |
| 4,801,688 | 1/1989 | Laguzza et al. . | |
| 4,867,973 | 9/1989 | Goers et al. ...................... | 424/85.91 |
| 4,868,106 | 9/1989 | Ito et al. ........................... | 435/7 |
| 4,925,648 | 5/1990 | Hansen et al. ..................... | 424/1.1 |
| 4,950,738 | 8/1990 | King et al. ........................ | 530/322 |
| 5,045,451 | 9/1991 | Uhr et al. .......................... | 435/7.23 |
| 5,057,302 | 10/1991 | Johnson et al. ................... | 424/85.9 |
| 5,066,789 | 11/1991 | Srinivasan et al. ................ | 530/388 |
| 5,106,951 | 4/1992 | Morgan et al. .................... | 530/391.9 |
| 5,206,370 | 4/1993 | Schwartz et al. .................. | 546/281 |

FOREIGN PATENT DOCUMENTS

| | | |
|---|---|---|
| 0175617 | 3/1986 | European Pat. Off. . |
| 0188256 | 7/1986 | European Pat. Off. . |
| 0203764 | 12/1986 | European Pat. Off. . |
| 0328147 | 8/1989 | European Pat. Off. . |
| 87/06837 | 5/1987 | WIPO . |
| 88/02594 | 10/1987 | WIPO . |

OTHER PUBLICATIONS

Kalofomo et al., The Journal of Nuclear Medicine, vol. 31, No. 11, pp. 1791–1796 (1990).
Hermentin et al. Behring Inst. Mitt, No. 82, pp. 197–215 (1988).
Harris et al., TIBTECH, vol. 11, pp. 42–44 (1993).
Borrebaeck, Journal of Immunological Methods, vol. 123, pp. 157–165 (1989).
Waldmann, Science, vol. 252, pp. 1657–1662 (1991).
Parker (ed.), Radioimmunoassay of Biologically Active Compounds, Prentice–Hall, Inc., Englewood Cliffs, New Jersey, p. 93 (1976).
Van Vunakis et al. (eds.), Methods in Enzymology, vol. 70, Immunochemical Techniques, Academic Press, New York, 1980, p. 101 (1980).
King et al., "Preparation of Protein Conjugates via Intermolecular Hydrazone Linkage," Biochemistry 1986, 25, 5774–5779.
Seventy–Ninth Annual Meeting of the American Association for Cancer Research, May 25–28 1988, Proceedings, New Orleans, vol. 29, Mar. 1988, p. 288.
Kravolec et al., "Synthesis of site–specific methotrexate–IgG conjugates," Cancer Immunol. Immunoether (1989) 29: 293–302.

*Primary Examiner*—Margaret Parr
*Assistant Examiner*—F. Christopher Eisenschenk
*Attorney, Agent, or Firm*—Stoel Rives

[57] ABSTRACT

Targeting substance-diagnostic/therapeutic agent conjugates joined by stabilized Schiff base or hydrazone linkages are disclosed. In addition, slow release carrier-drug pharmaceuticals are described. The diagnostic and therapeutic conjugates and pharmaceuticals of the present invention provide certain advantages relating to in vivo administration, including controlled release of the active agent at a target site.

17 Claims, No Drawings

TARGETING SUBSTANCE-DIAGNOSTIC/THERAPEUTIC AGENT CONJUGATES HAVING SCHIFF BASE LINKAGES AND METHODS FOR THEIR PREPARATION

This application is a division of application No. 07/987,535, filed Dec. 7, 1992, now abandoned, which is a continuation of application No. 07/714,806, filed Jun. 13, 1991, now abandoned, which is a division of application No. 07/415,154, filed Sep. 29, 1989, now U.S. Pat. No. 5,066,789, which is a continuation-in-part of application No. 07/252,298, filed Sep. 30, 1988, now abandoned.

TECHNICAL FIELD

The claimed invention relates to targeting substance-diagnostic/therapeutic agent conjugates that are joined by improved Schiff base or hydrazone linkages that provide advantageous properties for in vivo imaging and therapy.

BACKGROUND OF THE INVENTION

A Schiff base is an imine condensation product of an aldehyde and a primary amine. Formation of a Schiff base may be illustrated by the following reaction:

$$R-CHOH-CH_2OH \xrightarrow{NaIO_4} R-CHO + NH_2-R' \longrightarrow$$

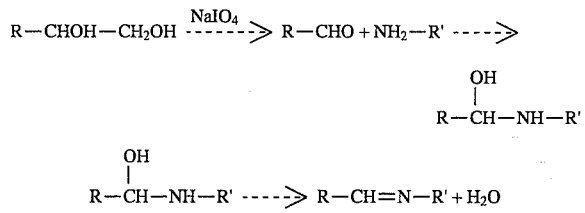

Where R and/or R' are aliphatic substituents, the C=N (imine) bond of a Schiff base is known to be very unstable. Typically, the C=N bond is stabilized by reduction with sodium borohydride or sodium cyanoborohydride, as represented by the following reaction:

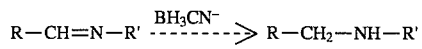

Stabilization of the C=N bond may also be achieved through the attachment of an aryl(s) to the imine carbon or nitrogen, or if a hydroxyl or second nitrogen is bonded to the imine nitrogen.

Schiff base linkages have been used for conjugation of glycoproteins in general, and for conjugation of immunoglobulins in particular. In a typical reaction scheme, oligosaccharide moieties present on an immunoglobulin molecule are oxidized to form one or more aldehyde groups. The resultant immunoglobulin aldehyde(s) is reacted with a primary amine to form a Schiff base, which is then stabilized by reduction.

A prototypical Schiff base conjugation procedure (as described above) suffers from numerous disadvantages. First, the immunoglobulin (glycoprotein) molecule is subjected to harsh oxidizing conditions in order to generate free aldehyde groups. This harsh oxidation may impair the biological activity of the immunoglobulin molecule, especially in instances where complete oxidation of all carbohydrate residues is desired. Second, stabilization of the Schiff base conjugate is accomplished through exposure of the conjugate to a harsh reducing agent, which also may adversely affect the biological function of the immunoglobulin moiety. Third, the number of substituents that may be conjugated by Schiff base linkage to immunoglobulin aldehyde groups is limited by the number of carbohydrate moieties present on a particular immunoglobulin molecule. For instance, the amount of carbohydrate present on an immunoglobulin molecule may vary between 2–3% for IgG and 9–12% for IgM, IgD and IgE (I. M. Roitt et al., "Immunology", Gower Medical Publishing Ltd., 1985, p. 5.2).

Alternatively, an aldehyde generated on an immunoglobulin molecule may be reacted with a hydrazide to form a hydrazone, according to the following reaction scheme:

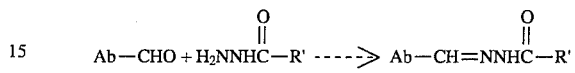

Hydrazones are more stable than Schiff bases formed by the reaction of an aldehyde and a primary amine, and thus do not require reduction after formation of the linking bond. However, this reaction scheme suffers from several disadvantages: (1) the immunoglobulin must still be oxidized to generate free aldehyde groups; and (2) the degree of conjugation is limited by the number of carbohydrate moieties present on the immunoglobulin molecule.

SUMMARY OF THE INVENTION

The present invention provides targeting substance conjugates covalently bonded to one or more diagnostic or therapeutic agents through improved Schiff base linkages. Oxidation/reduction of the targeting substance component is eliminated, and the number of attached agents per targeting substance may be increased. In addition, a variety of targeting substance substituents may be used to produce a stable Schiff base-linked conjugate of the claimed invention. While the disclosed Schiff base linkages provide a certain degree of conjugate stability, the linkages are cleavable and may advantageously permit release of attached agent at a target site.

Another aspect of the invention includes targeting substance—diagnostic/therapeutic agent conjugates joined by an aromatic, heterobifunctional Schiff base linker. These aryl-substituted Schiff base linkages also provide increased conjugate stability. In one embodiment, the aryl-substituted Schiff base linkage is formed between the targeting substance and the linker. In a second embodiment, the aryl-substituted Schiff base linkage is formed between the agent and the linker. The latter linker may further provide enhanced target cell retention of the conjugate.

DETAILED DESCRIPTION OF THE INVENTION

Prior to setting forth the invention, it may be helpful to set forth definitions of certain terms to be used within the disclosure.

Schiff base linkage: A chemical bond represented by R—CH=NH—R'.

Stabilized Schiff base linkage: A chemical bond represented by R—CH=NNHCOR' (hydrazone).

Conventional Schiff base linkage: A Schiff base linkage formed by reaction of an aldehyde or ketone group present on a targeting substance with a nucleophilic primary amine or hydrazide present on a diagnostic or therapeutic agent.

Unique Schiff base linkage: A Schiff base linkage formed by reaction of: (1) an endogenous or chemically added primary amine or hydrazide present on a targeting substance with (2) an endogenous or chemically added aldehyde or ketone present on a diagnostic or therapeutic agent.

Targeting substance: A moiety that binds to a defined population of cells. For instance, "targeting substance" includes targeting proteins and peptides capable of binding receptors, enzymatic substrates, antigenic determinants, or other binding sites present on a target cell population. As used herein, "targeting substance" also includes non-proteinaceous moieties.

Conjugate: A hybrid molecule wherein the components are joined by one or more covalent chemical linkages.

Targeting substance conjugate: A conjugate wherein one component is a targeting substance, and more preferably, is an antibody (i.e., an immunoconjugate). Typically, the second component of a targeting substance conjugate is a therapeutic agent (i.e., a drug, a toxin or a radionuclide) or a diagnostic agent (i.e., a radionuclide). "Targeting substance conjugate" includes both targeting substance-agent conjugates and targeting substance-carrier-agent conjugates.

A first aspect of the present invention describes a conjugate of a targeting substance and a diagnostic or therapeutic agent covalently joined through one or more stabilized Schiff base linkages.

In a first aspect of the claimed invention, a targeting substance conjugate is joined through a stabilized unique Schiff base linkage, as represented below:

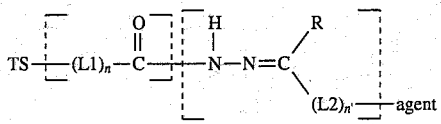

wherein
- "TS" is a targeting substance (such as a targeting protein, peptide, polypeptide, glycoprotein, carbohydrate-free protein; a targeting substance-carrier; or a targeting substance-chelator);
- "L1" and "L2" are derived from a heterobifunctional linker having a hydrazide or aldehyde/ketone active group at one end of the linker in its unreacted state;
- "n" and "n'" are 0 or 1;
- "R" is H; an alkyl, aryl, or alicyclic substituent; and
- "agent" is a diagnostic or therapeutic agent useful for in vivo applications, or a chelating agent capable of binding small diagnostic or therapeutic molecules.

The bracketed portion of the targeting substance conjugate represents the stabilized Schiff base linkage that results from reaction of linker hydrazide and linker aldehyde/ketone.

Preferred targeting substances useful within the present invention include antibody and antibody fragments; peptides, such as bombesin, gastrin-releasing peptide, RGD peptide, substance P, neuromedin-B, neuromedin-C, and metenkephalin; and hormones, such as EGF, α- and β-TGF, estradiol, neurotensin, melanocyte stimulating hormone, follicle stimulating hormone, luteinizing hormone, and human growth hormone. Biotin, avidin, proteins corresponding to known cell surface receptors (including low density lipoproteins, transferrin, insulin and $CD_4$), fibrinolytic enzymes, and biological response modifiers (including interleukin, interferon, erythropoietin and colony-stimulating factor) are also preferred targeting substances. Analogs of the above-listed targeting substances that retain the capacity to bind to a defined target cell population may also be used within the claimed invention. In addition, synthetic targeting substances may be designed by peptide synthetic or recombinant DNA techniques.

Exemplary cytotoxic agents include toxins and drugs. Several of the native toxins useful within the present invention consist of an A and a B chain. The A chain is the cytotoxic portion and the B chain is the receptor-binding portion of the intact toxin molecule (holotoxin). Because toxin B chain may mediate non-target cell binding, it is often advantageous to conjugate only the toxin A chain to a targeting substance. However, while elimination of the toxin B chain decreases non-specific cytotoxicity, it also generally leads to decreased potency of the toxin A chain-targeting substance conjugate, as compared to the corresponding holotoxin-targeting substance conjugate.

One possible explanation for the decreased potency of A chain-targeting substance conjugates is that B chain is required for translocation of the A chain across endosomic membranes into the target cell cytoplasm. In the absence of translocation, the targeting substance conjugate remains in the interior of an endosome, and is ultimately transported to a lysosome. Within the lysosome, the targeting substance conjugate is degraded, and thus the A chain cytotoxic agent fails to reach its cytoplasmic target site. The decreased potency associated with toxin A chain-targeting substance conjugates also accompanies the use of ribosomal inactivating protein-targeting substance conjugates. Ribosomal inactivating proteins (RIPs) are naturally occurring protein synthesis inhibitors that lack translocating and cell-binding ability.

Within the present invention, preferred toxins include holotoxins, such as abrin, ricin, modeccin, Pseudomonas exotoxin A, Diphtheria toxin, pertussis toxin and Shiga toxin; and A chain or "A chain-like" molecules, such as ricin A chain, abrin A chain, modeccin A chain, the enzymatic portion of Pseudomonas exotoxin A, Diphtheria toxin A chain, the enzymatic portion of pertussis toxin, the enzymatic portion of Shiga toxin, gelonin, pokeweed antiviral protein, saporin, tritin, barley toxin and snake venom peptides.

Exemplary drugs include daunomycin, adriamycin, vinblastine, doxorubicin, bleomycin, methotrexate, 5-fluorouracil, 6-thioguanine, cytarabine, cyclophosphamide and similar conventional chemotherapeutics as described in *Cancer: Principles and Practice of Oncology*, 2d ed., V. T. DeVita, Jr., S. Hellman, S. A. Rosenberg, J.B. Lippincott Co., Philadelphia, Pa., 1985, Chapter 14. Yet another preferred drug within the present invention belongs to the trichothecene family, with verrucarin A particularly preferred. Experimental drugs may also be suitable for use within the present invention (see, e.g., *NCI Investigational Drugs, Pharmaceutical Data* 1987, NIH Publication No. 88-2141, Revised November 1987).

Conjugates of targeting substances and cytotoxic agents joined through non-stabilized unique Schiff base linkages have been described (Sela et al., U.S. Pat. Nos. 4,093,607 and 4,263,279). Such unique Schiff base conjugates may be represented by the following formula:

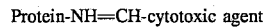

which upon reduction yields:

A stabilized unique Schiff base-linked targeting substance conjugate of the present invention, as described above, provides certain advantages as compared to previously described non-stabilized, reduced unique Schiff base conjugates:

(1) Various substituents of the targeting substance may be used to produce a stabilized unique Schiff base-linked conjugate of the claimed invention. For instance, a native disulfide bond within the targeting substance may be used to generate a free sulfhydryl, which in turn reacts with a maleimide end of a heterobifunctional linker having a hydrazide or aldehyde group present at the other end of the linker molecule. If the targeting substance does not possess a native disulfide bond, lysine residues may be used to introduce free sulfhydryl groups into the targeting substance through reaction with iminothiolane. Alternatively, targeting substance lysines may be linked to a heterobifunctional reagent having a free hydrazide or aldehyde group available for conjugation with an active agent. In yet another embodiment of the invention, targeting substance carboxylic acid groups may be reacted with hydrazine to form a targeting substance hydrazide. Thus, either sulfhydryls, lysines or carboxylic acid groups of a targeting substance may be used for production of unique Schiff base-linked targeting substance conjugates described herein.

In contrast, a non-stabilized unique Schiff base linkage according to Sela et al. requires binding of periodate-oxidized drug to free amino groups of protein to form a non-stabilized imine linkage, which must be stabilized by borohydride reduction.

(2) Formation of a stabilized unique Schiff base (hydrazone) linkage according to the present invention does not require reduction of the resultant conjugate for stabilization. The non-stabilized unique Schiff base (imine) conjugate schematically represented above must be reduced with sodium borohydride or sodium cyanoborohydride for stabilization of the imine bond. Reduction of the imine bond to an amine bond makes the linkage non-cleavable under biologic conditions. In addition to reduction of the imine bond to an amine bond, exposure to borohydride or cyanoborohydride may also reduce disulfide bonds and amide linkages, and produce other as yet unidentified deleterious effects on the protein or diagnostic/therapeutic agent component of the conjugate.

In one embodiment of this aspect of the invention, lysine groups of a targeting substance (whether having or lacking endogenous carbohydrate residues) are treated with a reagent (for instance, iminothiolane) that adds free sulfhydryl groups to the targeting substance. The sulfhydryl-derivatized targeting substance (TS-SH) is then reacted with a heterobifunctional linker having a maleimide reactive group.

An exemplary heterobifunctional linker in this regard has a maleimide reactive group at one end and a hydrazide reactive group at the other end. One example of a heterobifunctional linker useful in this regard is:

Formula 1 which may be obtained by the following reaction scheme:.

Alternatively, the maleimide group of the described heterobifunctional linker may be reacted with native sulfhydryl groups on the targeting substance. Native sulfhydryls may be generated from targeting substance disulfide bonds through exposure of the targeting substance to a reducing agent, such as dithiothreitol.

The free hydrazide group of the targeting substance-linker molecule may then be reacted with aldehyde or ketone groups of a diagnostic or therapeutic agent. One technique through which aldehyde or ketone groups may be generated on a diagnostic/therapeutic agent is oxidation of oligosaccharides (in the case of a carbohydrate-containing agent). With certain diagnostic/therapeutic agents, oxidation of the agent may provide additional in vivo benefits. For instance, oxidation of ricin A chain decreases delivery of ricin A to the mammalian liver.

A method for generating aldehyde/ketone groups on a non-carbohydrate-containing agent involves oxidation of methyl groups or primary hydroxyl groups to form aldehydes, or oxidation of secondary hydroxyl groups to form ketones. For example, the secondary hydroxyl group at the 2' position of the macrocyclic ring of verrucarin A may be oxidized to a ketone. Reaction of the targeting substance-linker and oxidized agent may be represented by the following scheme:

$$TS-L1-N(H)-NH_2 + O=C(H)-Agent \longrightarrow$$

$$TS-L1-N(H)-N=C(H)-Agent$$

Alternatively, an aldehyde group may be introduced into a non-carbohydrate-containing diagnostic or therapeutic agent through use of a heterobifunctional linker having a free reactive aldehyde at one end. An example of a heterobifunctional linker useful in this regard is:

Formula 2 which may be obtained by the following reaction scheme:

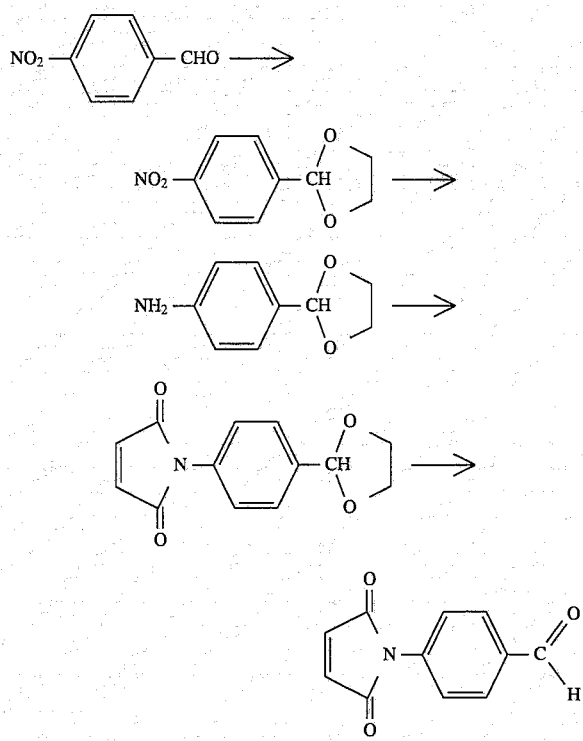

The maleimide group of this heterobifunctional linker reacts with native sulfhydryl groups on the diagnostic or therapeutic agent (generated through treatment with a reducing agent) or with a sulfhydryl-derivatized agent (iminothiolane-generated sulfhydryls from native lysines of the agent).

The free hydrazide group of the targeting substance-linker molecule is then reacted with the aldehyde group of the agent-linker molecule, forming a stabilized unique Schiff base-linked targeting substance conjugate. This reaction is schematically illustrated below:

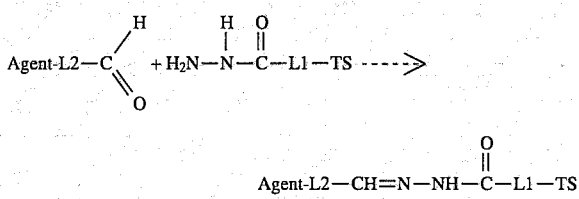

Another heterobifunctional linker useful in this regard has a free reactive aldehyde at one end and an N-hydroxysuccinimide ester at the other end. An exemplary linker in this regard includes:

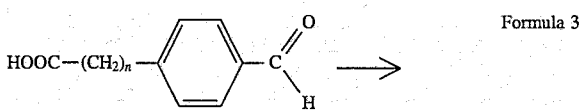

Formula 3

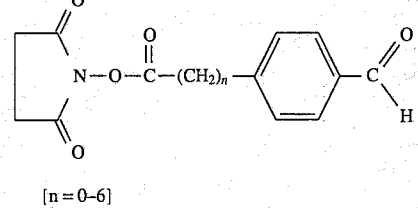

[n = 0–6]

Lysines of the diagnostic or therapeutic agent react with the N-hydroxysuccinimide ester of the linker molecule. The free hydrazide group of the targeting substance is then reacted with the aldehyde group of the agent-linker molecule, as described above.

In a second embodiment of the present invention, a targeting substance is reacted with a heterobifunctional linker having a maleimide reactive group at one end and an aldehyde reactive group at the other end. An example of a heterobifunctional linker useful in this regard has been provided above. The maleimide group of the linker reacts with sulfhydryl groups of a targeting substance (generated as described above).

A diagnostic or therapeutic agent is converted into an agent-hydrazide through reaction with a maleimide-hydrazide heterobifunctional linker (as described previously). The free aldehyde group of the targeting substance-linker is then reacted with the diagnostic/therapeutic agent-linker hydrazide, yielding a targeting substance conjugate according to the following scheme:

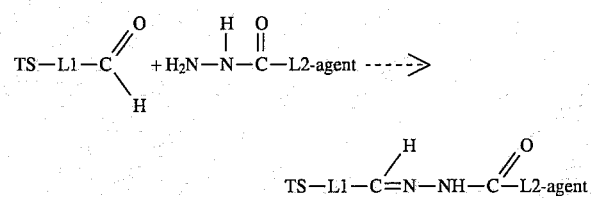

The second embodiment also includes oxidation of a polysaccharide carrier, such as dextran, to provide several free aldehyde groups. Diagnostic or therapeutic agents that have been converted to agent-hydrazide are then reacted with free aldehyde present on the oxidized carrier molecule, thereby forming a stabilized Schiff base-linked carrier-agent conjugate. The carrier-agent conjugate is then covalently attached to a targeting substance, for instance by SMCC linkage to targeting substance sulfhydryls. Alternatively, an amino-form of dextran is first derivatized with SMCC, then subjected to limited oxidation to generate free aldehyde groups. The oxidized SMCC-dextran is subsequently reacted with agent-hydrazide, then covalently attached to targeting substance sulfhydryls. By limiting oxidation of dextran, unoxidized sugars remaining on the dextran molecule will serve to increase solubility of the targeting substance-carrier-agent conjugate. In some instances, it may be preferable to react oxidized SMCC-dextran with targeting substance-hydrazide and agent sulfhydryls.

In a third embodiment of the first aspect of the present invention, carboxylic acid groups of a targeting substance are directly derivatized with hydrazine in the presence of carbodiimide to form a targeting substance hydrazide. The targeting substance hydrazide is then covalently attached through a stabilized unique Schiff base linkage to an aldehyde or ketone group present on a diagnostic or therapeutic agent. The following reaction scheme illustrates production of the resultant stabilized unique Schiff base-linked targeting substance conjugate:

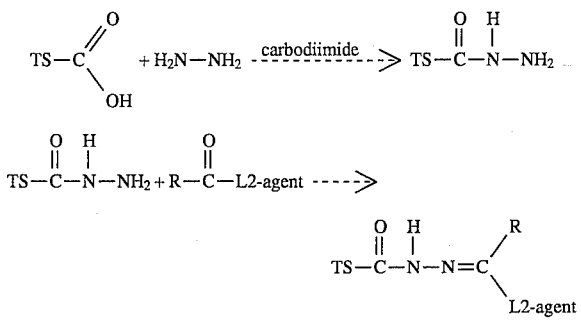

A variety of carbodiimides may be used as catalysts in the above reaction scheme, but 1-ethyl-3(3-dimethylaminopropyl)carbodiimide is a particularly preferred carbodiimide.

As depicted in the above reaction scheme, an aldehyde group may be introduced into either a carbohydrate- or non-carbohydrate-containing diagnostic or therapeutic agent through use of a heterobifunctional linker having a free reactive aldehyde at one end. In this illustrative example, L2 is present (n=1). Alternatively, aldehyde or ketone group(s) on the diagnostic/therapeutic agent may be obtained directly by oxidation of oligosaccharides (in the case of a carbohydrate-containing agent) or oxidation of methyl or secondary hydroxyl groups. When oxidation is used to generate aldehyde/ketone groups on the agent, L2 is not present (n=0).

Crosslinking of targeting substance during reaction with hydrazine is minimized by maintaining the concentration of targeting substance at approximately 2 mg/ml, and by using an excess of hydrazine reactant.

A comparison of the Schiff base-linked conjugates of the first aspect of the claimed invention and known Schiff base-linked conjugates highlights the following advantages provided by the conjugates described herein: (1) Neither the targeting substance nor the diagnostic or therapeutic agent need contain endogenous carbohydrate residues. (2) If the targeting substance and/or the diagnostic or therapeutic agent component of the conjugate contains endogenous carbohydrate, the carbohydrate moiety need not be subjected to oxidizing conditions in order to generate a Schiff base-linked conjugate. This is in contrast to previously described Schiff base-linked conjugates, which require generation of oxidized carbohydrate moieties. (3) Either sulfhydryl, ε-amino or carboxylic acid groups of the targeting substance may be derivatized in readiness for unique Schiff base-linkage of the agent. (4) In contrast to previously described Schiff base-linked conjugates which require oxidized oligosaccharide moieties, the degree of conjugation of the targeting substance or diagnostic or therapeutic agent of the present invention may be controlled (for instance, through the amount of hydrazide or linker substituted onto the targeting substance and/or agent components). Where Schiff base-linked conjugates are obtained using oxidized oligosaccharides, the degree of conjugation is directly related to the amount of carbohydrate natively associated with targeting substance or diagnostic or therapeutic agent, as well as the degree of oligosaccharide oxidation. (5) Stabilized Schiff base conjugates of the claimed invention need not be subjected to reducing conditions in order to stabilize the imine bond. (6) An increased number of diagnostic or therapeutic agents may be attached to targeting substance using the stabilized unique Schiff base linkages described herein. A second aspect of the present invention involves a targeting substance—diagnostic/therapeutic agent conjugate joined through a heterobifunctional, aromatic Schiff base linker. In a first embodiment of this aspect of the invention, a targeting substance conjugate has the following formula:

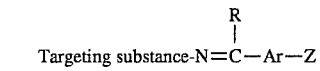

wherein

"Ar" is a substituted or unsubstituted aryl group derived from an aromatic aldehyde or ketone having the formula R—CO—Ar;

"N" is a nitrogen atom contributed by the targeting substance;

"C" is a carbon atom contributed by the aromatic aldehyde or ketone;

"R" is H or an alkyl, aryl or heteroaryl substituent contributed by the aromatic aldehyde or ketone; and "Z" is a diagnostic or therapeutic agent attached either directly or indirectly to Ar.

Preferred Ar groups in this regard include monocyclic aromatic rings, annulated aromatic rings, carbocyclic aromatic rings and heterocyclic ring systems. Particularly preferred Ar groups include substituted and unsubstituted benzene, furan, pyrrole, thiophene, pyridine, oxazole, imidazole, thiazole and annulated derivatives thereof. A preferred annulated Ar contains 2 to 5 rings.

According to this aspect of the claimed invention, aromatic aldehydes or aromatic ketones are designed and synthesized to act as reversible, acid cleavable linkers useful for controlled release of a diagnostic or therapeutic agent from a targeting substance-diagnostic/therapeutic agent conjugate. It is contemplated that the stability of the Schiff base (imine) linkage depicted above may be modified by altering the electron-withdrawing or electron-donating nature of the linker aromatic ring.

Previously, procedures for Schiff base conjugation of a protein and a carbonyl compound required a final reductive step (reductive amination) for stabilization of the resultant imine linkage. Alternatively, in the case of α-hydroxy aldehydes (such as glyceraldehyde) or glucose, the Schiff base would undergo rearrangement to achieve a more stable product (Amadori rearrangement).

In contrast to previously described Schiff base linkages between protein and an aldehyde or ketone compound, the claimed targeting substance conjugate does not require stabilization of the Schiff base linkage (either through reduction or rearrangement). Instead, unreduced imine bond stability is achieved by altering the electron-withdrawing or electron-donating characteristics of the linker aromatic ring substituents. For instance, substitution of ortho-hydroxy groups and/or electron-donating groups on the aromatic ring of the Schiff base linker would increase the lability of the imine bond linkage to acidic conditions. Electron-withdrawing substituents on the aromatic ring of the Schiff base linker would stabilize the imine bond linkage to acidic conditions.

Preferred electron-donating groups in this regard include $O^-$, $S^-$, $NR'_2$, $NHR'$, $NH_2$, $NHCOR'$, $OR'$, $OH$, $OCOR'$, $SR'$, $SH$, $Br$, $I$, $Cl$, $F$ and $R'$. Preferred electron-withdrawing groups in this regard include $NO_2$, $CN$, $CO_2H$, $CO_2R'$, $CONH_2$, $CONHR'$, $CONR'_2$, $CHO$, $COR'$, $SO_2R'$, $SO_2OR'$ and $NO$. Within the electron-donating and electron-withdrawing groups, R' may be H; a substituted or unsubstituted alkyl, aryl or heteroaryl group; a substituent that increases water solubility of the linker; or a substituent that further affects the stability of the resultant Schiff base linkage.

Within the second aspect of the invention, "Z" indicates a diagnostic or therapeutic agent that is either directly or indirectly attached to Ar. Preferred Z substituents include a directly-linked radionuclide; a functional group suitable for linking a cytotoxic agent; a chelating ligand capable of binding a radiometal; and an organometallic substituent, such as aryltin, that is susceptible to replacement by a radiohalogen.

The Ar group of the linker may be derivatized with a Z substituent prior to covalent linkage of a targeting substance amine group and an aldehyde or ketone moiety present on Ar (generating a unique Schiff base linkage). If Z is a functional group suitable for linking a cytotoxic agent, a chelating ligand capable of binding a radiometal, or an organometallic substituent, the Z substituent may be reacted with a cytotoxic agent, a radiometal or a radiohalogen subsequent to conjugation of Ar—Z and a targeting substance.

Alternatively, the Z substituent of the aromatic linker of the second aspect of the invention may be first reacted with a cytotoxic agent, a radiometal or a radiohalogen, thereby forming an R—CO—Ar—[Z]-diagnostic/therapeutic agent compound. "[Z]" indicates that the prereaction Z substituent may or may not remain after reaction of Z with the diagnostic or therapeutic agent. The R—CO—Ar—[Z]-diagnostic/therapeutic agent compound is then conjugated with a targeting substance via a Schiff base linkage formed between the R—CO—Ar group of the linker and a targeting substance amine group.

Preferred Z functional groups include activated esters (which react with amino groups), maleimides (which bind to sulfhydryl groups) and haloacetamides (which also bind to sulfhydryl groups). In a particularly preferred embodiment, Z is an N-hydroxysuccinimide ester, which possesses electron-withdrawing properties that increase the acid stability of the Schiff base linkage between the targeting substance and the Ar group. In another particularly preferred embodiment, Z is a bromoacetamide group, which has electron-donating characteristics that decrease the acid stability of the Schiff base linkage of the conjugate.

Exemplary bifunctional linkers and their corresponding synthetic routes are shown below:

Preferred Z chelating ligands include radionuclide metal chelates as described in Fritzberg, EP 188,256. Particularly preferred chelates in this regard have a free $NH_2$ group capable of reaction with Z when Z is an activated ester or have an available maleimide group capable of reaction with Z when Z is a sulfhydryl. Yet another preferred Z is an aryltin group, as described in Wilbur et al, EP 203,764, with tributyltin particularly preferred. Radiohalogens may then be attached to linker substituent Ar by halo-destannylation.

Z may also represent a radionuclide directly attached to the Ar linker substituent, with $^{125}I$ p-iodobenzaldehyde a particularly preferred Ar—Z compound. Appropriately substituted aromatic compounds that have been directly radio-iodinated by addition of electrophilic iodine are also preferred Ar—Z compounds. For instance, the hydroxy group of o-vanillin activates an Ar ring for electrophilic attack by a radiohalogen (i.e., iodine). O-vanillin offers the further advantage of regioselective radiohalogenation, since both Ar ring positions ortho to the activating hydroxy group are occupied (see formula below).

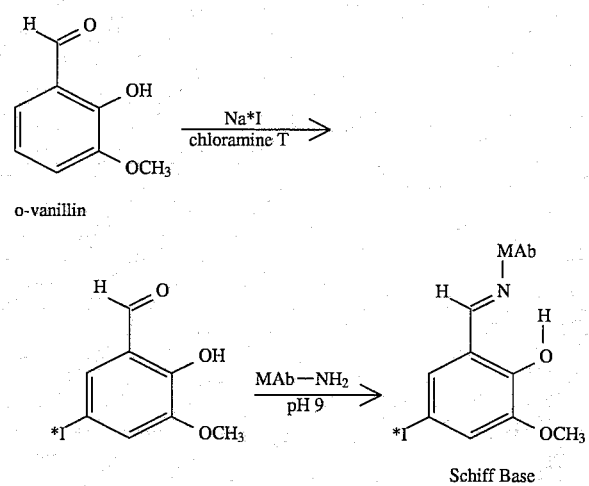

Preferred diagnostic and therapeutic radionuclides that may be either directly or indirectly attached to Ar include gamma-emitters, positron-emitters, Auger electron-emitters, X-ray emitters and fluorescence-emitters, with beta- or Formula:

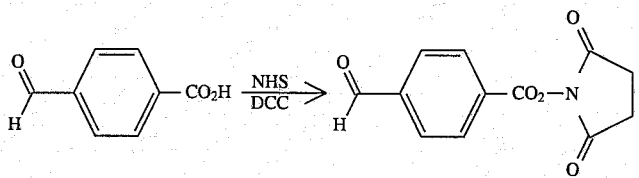

4

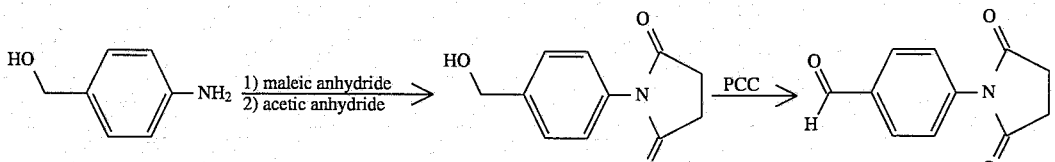

5

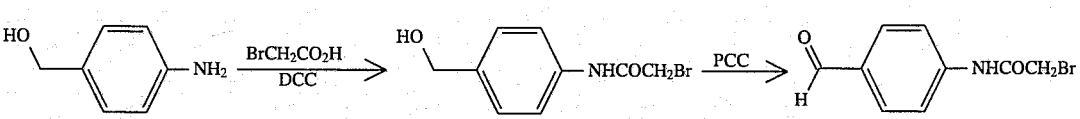

6 alpha-emitters preferred therapeutic agents. Radionuclides are well-known in the art and include $^{123}$I, $^{125}$I, $^{130}$I, $^{131}$I, $^{133}$I, $^{135}$I, $^{47}$Sc, $^{72}$As, $^{72}$Se, $^{90}$Y, $^{88}$Y, $^{97}$Ru, $^{100}$Pd, $^{101m}$Rh, $^{119}$Sb, $^{128}$Ba, $^{197}$Hg, $^{211}$At, $^{212}$Bi, $^{212}$Pb, $^{109}$Pd, $^{111}$In, $^{67}$Ga, $^{68}$Ga, $^{67}$Cu, $^{75}$Br, $^{76}$Br, $^{77}$Br, $^{90m}$Tc, $^{11}$C, $^{3}$N, $^{15}$O and $^{18}$F. Preferred therapeutic radionuclides include $^{188}$Re, $^{186}$Re, $^{203}$Pb, $^{212}$Pb, $^{212}$Bi, $^{109}$Pd, $^{64}$Cu, $^{67}$Cu, $^{90}$Y, $^{125}$I, $^{131}$I, $^{77}$Br, $^{211}$At, $^{97}$Ru, $^{105}$Rh, $^{198}$Au and $^{199}$Ag.

Intracellular release of a cytotoxic agent, a chelating ligand-plus agent or a radionuclide from a targeting substance conjugate may be desirable in many instances. In this regard, the claimed diagnostic or therapeutic targeting substance conjugates provide serum stability during delivery of the conjugate to an appropriate target cell. Upon internalization of the conjugate into target cell endosomes, the attached cytotoxic agent or radionuclide is released in the low pH environment, which in turn may facilitate translocation of the diagnostic or therapeutic agent or radionuclide from the target cell endosome into the cytoplasm. In the case of certain proteinaceous agents, translocation into the cytoplasm would allow the agent to escape degradation in target cell lysosomes.

Some proportion of administered targeting substance conjugate will bind to normal cells of the mammalian recipient. Typically, if antibody is conjugated to a radiometal using non-cleavable bifunctional linkers, accumulation of significant amounts of radionuclide in normal tissues (i.e., liver and bone marrow) by receptor-mediated endocytosis is observed.

In contrast, the conjugate of the second aspect of the invention provides a reversible (acid-cleavable) attachment of the diagnostic/therapeutic agent to a targeting substance. The claimed conjugate might provide reduced accumulation of the radionuclide in normal tissues, through release of the covalently attached radiometal into the acidic environment of the normal cell endosome/lysosome. As a result, the diagnostic/therapeutic agent (with or without chelator) may be subject to accelerated metabolism and excretion by the normal cell. When the agent is shunted out of the normal cell, it is returned to the bloodstream and rapidly excreted by the kidney, rather than accumulating in normal tissues.

In a second embodiment of the second aspect of the claimed invention, a targeting substance—diagnostic/therapeutic agent conjugate joined by a Schiff base linkage may be synthesized according to the following reaction scheme:

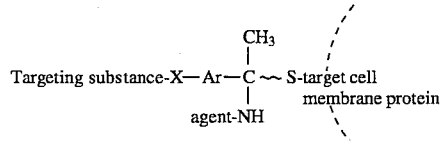

wherein

"X" is $(CH_2)_n$—Y, where n=0–6, Y=active ester, isothiocyanate or maleimide, and X is substituted at the 3 and/or 5 position of Ar;

"Ar" is aryl substituted with electron-donating and/or electron-withdrawing groups at the 2, 4 and/or 6 position;

"R" is H or an alkyl, aryl or heteroaryl substituent contributed by the aromatic aldehyde or ketone; and "agent" is an amino-containing diagnostic or therapeutic agent; an amino-containing chelator for a diagnostic or therapeutic agent; or an amino-containing aromatic organometallic.

In this second embodiment the resultant Schiff base linkage is formed between a diagnostic or therapeutic agent amine and a heterobifunctional, aromatic linker. This is in contrast to the Schiff base linkage of the first embodiment, which is formed between a targeting substance amine and a heterobifunctional, aromatic linker.

The effect of Ar substituents on the formation of Schiff base linkages and on conjugation to a targeting substance should be negligible. However, the rate of hydrolysis of the diagnostic or therapeutic agent from the targeting substance conjugate may be influenced by substituents. For instance, the presence of electron-donating groups at positions 2, 4, and/or 6 of Ar will enhance release of the agent from the conjugate under acidic conditions; the presence of electron-withdrawing groups at positions 2, 4 and/or 6 of Ar will retard or inhibit the release of the agent from the targeting substance conjugate.

Preferred electron-donating groups in this regard include O$^-$, S$^-$, NR'$_2$, NHR', NH$_2$, NHCOR', OR', OH, OCOR', SR', SH, Br, I, Cl, F and R'. Preferred electron-withdrawing groups in this regard include NO$_2$, CN, CO$_2$H, CO$_2$R', CONH$_2$, CONHR', CONR'$_2$, CHO, COR', SO$_2$R', SO$_2$OR' and NO. Within the electron-donating and electron-withdrawing groups, R' may be H; a substituted or unsubstituted alkyl, aryl or heteroaryl group; a substituent that increases water solubility of the linker; or a substituent that further enhances the stability of the resultant Schiff base linkage.

In this embodiment, the targeting substance conjugate is serum stable, but upon binding at a target cell surface may undergo gradual hydrolysis, releasing the attached agent. Alternatively, the targeting substance conjugate may be susceptible to thiol addition to the imine (C=N) bond, wherein the sulfur atom is provided by a disulfide-containing protein of the plasma membrane. Thiol addition to the C=N bond of the conjugate would result in hemithioaminal formation (depicted below).

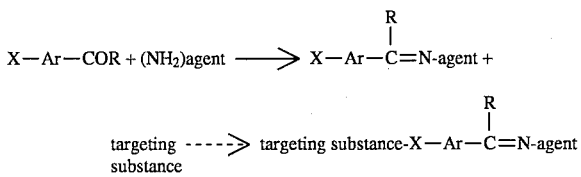

Any effect of Ar substituents on the reaction of the conjugate imine bond with cell surface sulfhydryl groups would be negligible.

Optimal in vivo diagnostic or therapeutic efficacy of targeting substance conjugates may involve three levels of conjugate-target cell membrane interaction: (1) binding of the conjugate to the cell surface membrane; (2) internalization of the conjugate into target cell endosomic vesicles; and (3) translocation of the conjugate from endosomic vesicles into the target cell cytoplasm.

Upon administration of the targeting substance conjugate of this embodiment of the second aspect of the invention, formation of a hemithioaminal would increase retention of the targeting substance conjugate at the cell surface through covalent attachment. Increased retention of the conjugate thus may result in increased internalization and translocation of the conjugate, which in turn may increase the efficacy of certain diagnostic/therapeutic agents. For radiotherapeutic conjugates, prolonged target cell retention increases the dose of radiation delivered to target cells.

In a third embodiment of the second aspect of the present invention, a targeting substance is attached to a diagnostic or therapeutic agent through use of a stabilized Schiff base/hydrazone linker, forming targeting substance conjugates as depicted below.

| Formula: |
|---|
| 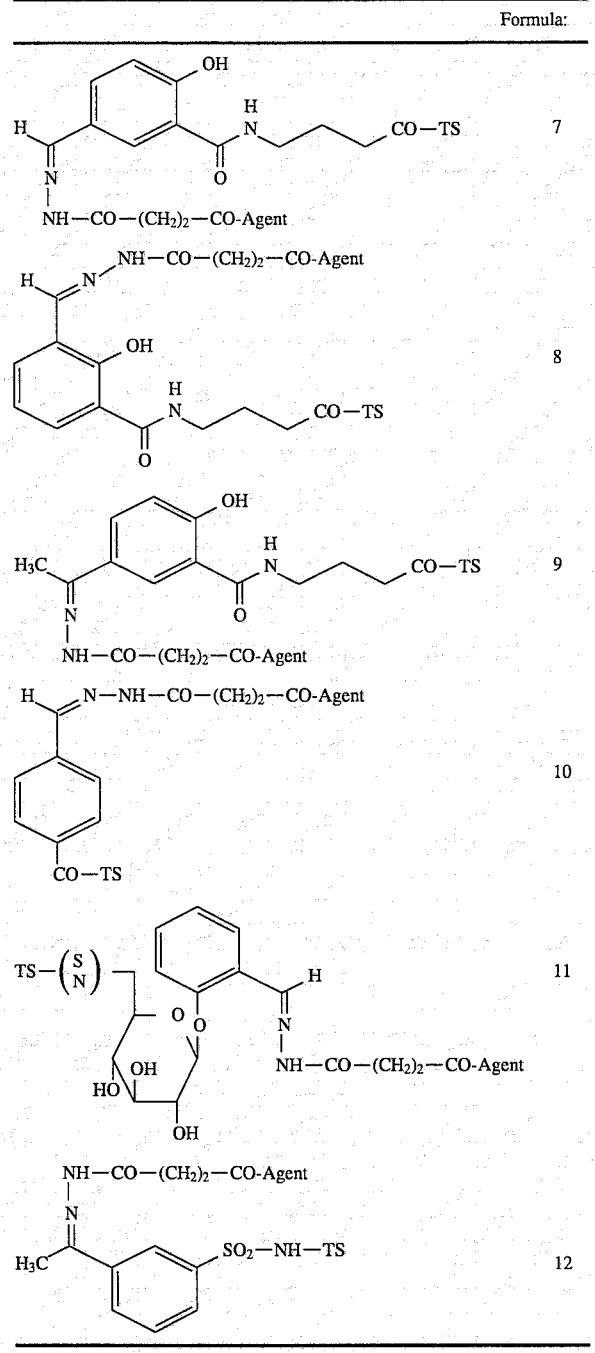 |

In the above schematics, "TS" is a targeting substance and "agent" is a diagnostic or therapeutic agent attached either directly or indirectly to the linker component of the above-depicted targeting substance conjugates; or a chelating agent capable of binding small diagnostic or therapeutic molecules, wherein the chelating agent is attached either directly or indirectly to the linker component depicted above.

Within this embodiment of the second aspect of the invention, the linking compounds serve as acid cleavable, heterobifunctional linkers useful for controlled release of a diagnostic or therapeutic agent/molecule at a target site. Heterobifunctional linkers may be derived from the following compounds:

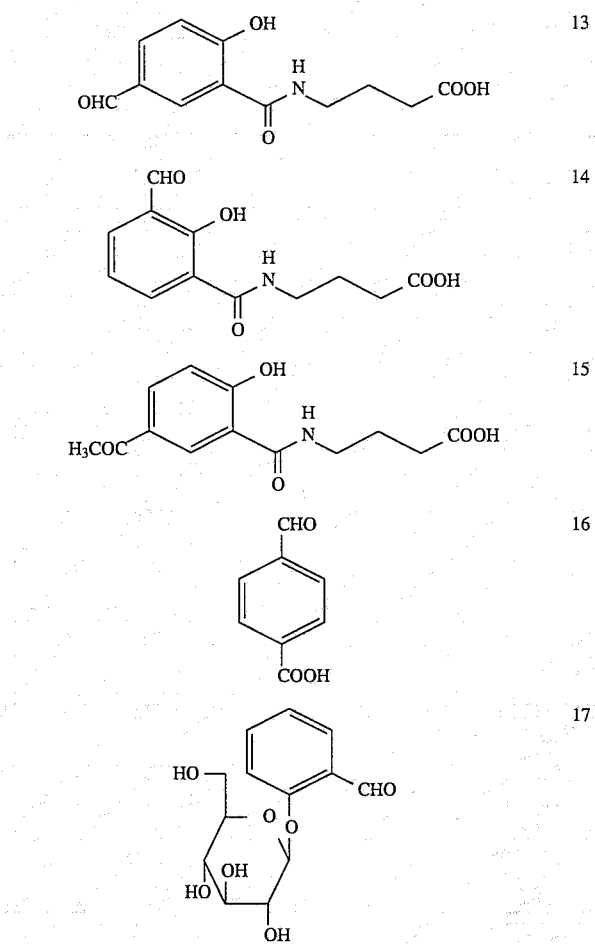

Linkers 13 and 14 may be synthesized according to the following reaction scheme:

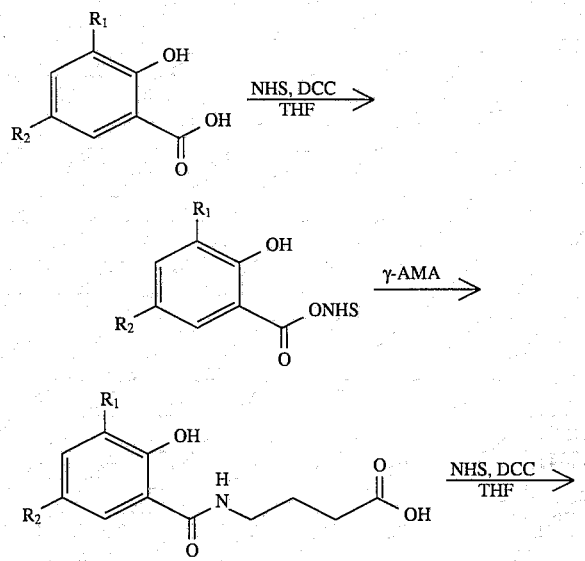

-continued

[Structure: benzene ring with R$_1$, OH, R$_2$ substituents and -C(=O)-NH-CH$_2$CH$_2$CH$_2$-C(=O)-ONHS side chain]

For linker 13, R$_1$=H and R$_2$=CHO; for linker 14, R$_1$=CHO and R$_2$=H; for linker 15, R$_1$=H and R$_2$=CH$_3$CO. Briefly, the carboxylic acid substituent of starting compound 13, 14 or 15 was converted into an N-hydroxysuccinimide (NHS) active ester. The NHS ester was displaced by gamma-amino butyric acid, which was then reacted with NHS to produce linkers which are ready for targeting substance conjugation.

More particularly, linkers 13, 14 and 15 were synthesized by reacting 1 eq. of starting compound in 50 ml tetrahydrofuran (THF) with 1 eq. NHS and 1 eq. dicyclohexylcarbodiimide (DCC). After 24 hours, the reaction was complete. The mixture was then filtered to remove DCU, the filtrate was then evaporated and triturated three times with ether to yield the NHS ester intermediate.

The NHS ester intermediate was dissolved in 25 ml dimethoxymethane and added to 25 ml H$_2$O containing 1 eq. of gamma-aminobutyric acid (Aldrich) and 1 eq. NaHCO$_3$. The reaction was complete in 16 hours. For synthesis of linker 14, however, 3 equivalents of gamma-aminobutyric acid were used to allow reaction with the aldehyde to form an imine. The product was then treated with 6N HCl to cleave the imine and yield the desired final product. For all three linkers, solvents were removed and the residue taken up in EtOAc and extracted with 1N HCl. EtOAc was dried using MgSO$_4$, filtered and evaporated to produce the desired linkers 13, 14 and 15.

Compound 16 was reacted with NHS and DCC in a similar manner to that described above for compounds 13–15 to form a heterobifunctional linker 16 suitable for use in targeting substance conjugation. Likewise compound 17 is converted to the 5'-tosylate heterobifunctional linker 17 by standard techniques that permit selective reaction at the 5' hydroxyl.

To summarize the examples that follow, Example I describes formation of a stabilized unique Schiff base targeting substance (monoclonal antibody) conjugate; Example II discusses a Stabilized unique Schiff base conjugate of human serum albumin and 16-oxo-verrucarin A. Synthesis of a targeting substance conjugate joined through an $^{125}$I benzaldehyde derivative linker is shown in Example III. Production of a targeting substance conjugate joined through a substituted aromatic aldehyde linker is described in Example IV. Acid-cleavable hydrazone linkers and corresponding targeting substance conjugates are examined in Example V.

The following examples are offered by way of illustration, and not by way of limitation.

EXAMPLE I

Formation of Stabilized Unique Schiff Base Targeting Substance Conjugate

A. Using Targeting Substance Sulfhydryls

Formation of a targeting protein hydrazide is achieved by treating monoclonal antibody (MAb; 5 mg/ml in phosphate-buffered saline [PBS], pH 8.5) with 10 mM dithiothreitol (DTT). The reaction mixture is agitated at room temperature for 30 minutes, and the reduced MAb is passed through a PD-10 column (Pharmacia, Uppsala, Sweden) to remove unreacted DTT.

The reduced monoclonal antibody is derivatized with a heterobifunctional linker of Formula 1. Any targeting substance containing one or more native disulfide bonds can thus be converted to a targeting substance hydrazide.

The trichothecene therapeutic agent 16-oxo verrucarin A is prepared by selenium dioxide oxidation of verrucarin A. The MAb hydrazide is then reacted with 16-oxo verrucarin A at 4C overnight with agitation, thereby yielding a unique Schiff base-linked targeting substance conjugate having the following structure:

$$\text{MAb}-\text{L1}-\overline{[-\overset{O}{\overset{\|}{C}}-\overset{H}{\overset{|}{N}}-N]}=\text{CH-agent}$$

B. Using Targeting Substance Lysines

Monoclonal antibody (5 mg/ml in PBS, pH 8.5) is treated with iminothiolane (IT); the amount of IT offered to the MAb preparation will be dependent upon the number of free MAb sulfhydryls desired. The reaction of IT with targeting substance lysines is schematically represented as follows:

$$\text{MAb}-\text{NH}_2 + \begin{array}{c}\text{H}_2\text{C}-\text{CH}_2\\ /\quad\quad\backslash\\ \text{H}_2\text{C}\quad\quad\text{C}=\overset{+}{\text{NH}_2}\text{Cl}^-\\ \backslash\quad/\\ \text{S}\end{array} \Longrightarrow$$

$$\begin{array}{c}\text{NH}_2\\ \text{H}\ |\\ \text{MAb}-\text{N}-\text{C}-\text{H}\\ |\\ \text{CH}_2\\ |\\ \text{CH}_2\\ |\\ \text{HS}-\text{CH}_2\end{array}$$

The reaction mixture is agitated at room temperature for 30 minutes, then passed through a PD-10 column to remove unreacted IT. The sulfhydryl-derivatized MAb is then reacted with a heterobifunctional linker Of Formula 1 to form a MAb hydrazide, as described in Example I.A.

Ricin A chain is oxidized with 10 mM NaIO$_4$, pH 5.5 at room temperature for 1 hour to generate free aldehyde groups from native ricin A oligosaccharide moieties. A significant advantage obtained through unique Schiff base linkage of ricin A aldehyde groups is that oxidation of ricin A decreases the amount of ricin A non-specifically delivered to the mammalian liver (as compared with non-oxidized ricin A).

The oxidized ricin A is then reacted with the MAb hydrazide produced above, yielding a unique Schiff base targeting substance conjugate having the following formula:

$$\text{MAb}-\text{L1}-\overline{[-\overset{O}{\overset{\|}{C}}-\overset{H}{\overset{|}{N}}-N]}=\overset{H}{\overset{|}{C}}\text{-ricin A}$$

Iminothiolane-derivatization may be used to generate free sulfhydryls on any lysine-containing protein or peptide. A heterobifunctional linker having a reactive maleimide on one end and a hydrazide group on the other end may then be used to form a proteinaceous hydrazide from a lysine-containing protein or peptide (i.e., regardless of whether the protein or peptide contains native disulfide bonds).

C. Using Targeting Substance Carboxylic Acid Groups

A solution of monoclonal antibody (2 mg/ml in PBS, pH 6.5) is reacted with excess hydrazine (1:150) and 1-ethyl- 3 (3-dimethylaminopropyl)-carbodiimide (1:100) and agitated for approximately 1 hour at room temperature to form a hydrazide of the MAb. Reaction conditions (reactant ratios and reaction time) may vary somewhat depending upon the monoclonal antibody used. At the end of the 1 hour incubation, the monoclonal antibody hydrazide is passed through a PD-10 column to remove unreacted hydrazine and 1-ethyl-3 (3-dimethylaminopropyl)-carbodiimide.

The reaction described directly introduces hydrazine onto the MAb, without the use of a heterobifunctional linker having a reactive hydrazine group. Dimerization (crosslinking) of MAb is prevented by maintaining a concentration of targeting substance (MAb) of approximately 2 mg/ml, and by using a large excess of hydrazine reactant. Further, the reaction described may be used with any targeting substance that contains one or more free carboxylic acid groups, whether glycoprotein or non-glycoprotein.

EXAMPLE II

Formation of Stabilized Unique Schiff Base Conjugate of Human Serum Albumin and Verrucarin A A solution of human serum albumin (HSA) is reacted with 1-ethyl-3(3-dimethyl-aminopropyl)-carbodiimide as in Example I.C. to form a hydrazide of HSA. These reaction conditions favor formation of the hydrazide with minimization of HSA crosslinking. The HSA hydrazide is then reacted with 16-oxo-verrucarin A, as described in Example I, to form a conjugate of HSA and 16-oxo-verrucarin A that is joined by a stabilized unique Schiff base linkage.

The drug-modified HSA may be used as a slow release agent, or alternatively, may serve as a drug carrier molecule suitable for conjugation with a targeting substance. In the latter case, HSA amines may be derivatized with succinimidyl-4-(N-maleimidomethyl) cyclohexane-1-carboxylate (SMCC) for linkage to targeting substance sulfhydryls.

EXAMPLE III

Synthesis of a Targeting Substance Conjugate Joined Through a $^{125}$I-Benzaldehyde Derivative Linker Radiolabeled benzaldehyde linkers demonstrate the relationship between aromatic aldehyde ring substituents and acid-catalyzed hydrolysis of Schiff base-containing radionuclide-targeting substance conjugates.

Briefly, $^{125}$I-p-iodobenzaldehyde was prepared as follows:

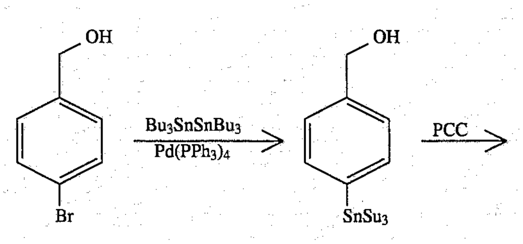

-continued

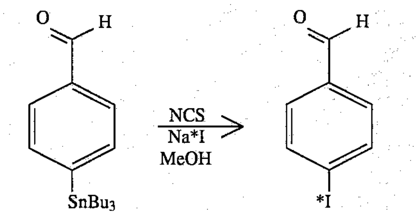

The tri-n-butyltin precursor to p-iodobenzaldehyde was prepared from commercially available p-bromobenzyl alcohol (Aldrich Chemical Co., Milwaukee, Wis.). Treatment of the p-bromobenzyl alcohol compound with hexabutylditin and $Pd(PPh_3)_4$ in toluene yielded the desired aryl tin compound. The alcohol was oxidized to the corresponding aldehyde with pyridinium chlorochromate (PCC) in methylene chloride solvent. The product was isolated in 69% yield after silica gel chromatography (ethyl acetate/hexanes) as a pale yellow oil. $^1$H NMR ($CDCl_3$) δ 0.83–1.61 (m, 27H); 7.64 (d, J=8 Hz, 2H); 7.78 (d, J=8 Hz, 2 Hz); 9.98 (s, 1H); $^{13}$C NMR ($CDCl_3$) δ 9.88, 13.82, 27.54, 29.25, 128.99, 129.59, 136.97, 137.50, 193.61.

A trace radiolabeling was accomplished with NCS/$^{125}$I to give the desired product, as evidenced by coinjection with a cold standard. The reaction conditions for labeling were as follows: To a solution of 0.05 mg of the benzaldehyde derivative in 0.05 ml of 1% acetic acid/MeOH was added approximately 360 μCi Na$^{125}$I and 0.0019 mg NaI carrier (1 mg/ml MeOH). To this mixture was added 17 μl of NCS (1 mg/ml in MeOH). After 30 minutes at room temperature, 17 μl of sodium bisulfite solution (0.72 mg/ml in water) was added to quench the reaction. The radiochemical yield obtained was 93%.

Upon conjugation of $^{125}$I-p-iodobenzaldehyde to monoclonal antibody NR-ML-05 (11:1 aldehyde:protein) at pH 9.0, 58% of the offered radiolabeled aldehyde was covalently attached to antibody.

The radionuclide-monoclonal antibody conjugate was purified by centrifugation (5,000 RPM, 10 min, room temperature) through a 30,000 MW microconcentrator (Amicon, Danvets, Mass.), yielding a conjugate of 97% purity by instant thin layer chromatography (ITLC). An analysis of specific activity of the purified conjugate indicated that approximately two lysine residues per antibody molecule had been modified.

Radiolabeled 5-iodo-3-methoxysalicylaldehyde and 5-iodo- 3-methylsalicylaldehyde (below) are prepared by radioiodination of o-vanillin and 3-methylsalicylaldehyde, respectively.

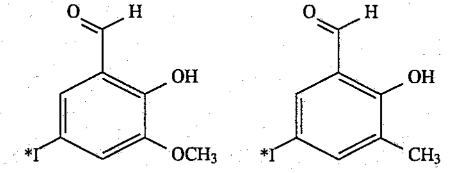

Radioiodination of o-vanillin and 3-methylsalicylaldehyde should be regioselective, since both positions ortho to the hydroxy substituent of the aromatic ring are occupied.

The iodinated aromatic aldehydes illustrated above should demonstrate decreased acid stability as compared to $^{125}$I-p-iodobenzaldehyde, since the ortho-hydroxy substituents can protonate a Schiff base linkage via an intramolecular mechanism. More particularly, the meta methoxy group of 5-iodo-3-methoxysalicylaldehyde has slight electron-withdrawing properties that may increase the acid stability of the Schiff base linkage; the meta methyl group of 3-methylsalicylaldehyde has electron-donating characteristics, which should decrease the stability of the Schiff-base-linked conjugate. Conjugates containing radiolabeled 5-iodo-3-methoxysalicylaldehyde and 5-iodo-3-methylsalicylaldehyde can be characterized as having "stable" conventional Schiff base linkages that are cleavable under mildly acidic conditions (pH 5–6),

EXAMPLE IV

Schiff Base-Linked Targeting Substance Conjugates Joined by a Substituted Aromatic Aldehyde Linker A stable Schiff base linkage between an amine and an aromatic carbonyl compound is formed using adriamycin and substituted or unsubstituted acetophenone or aromatic aldehyde. A representative reaction scheme is shown below:

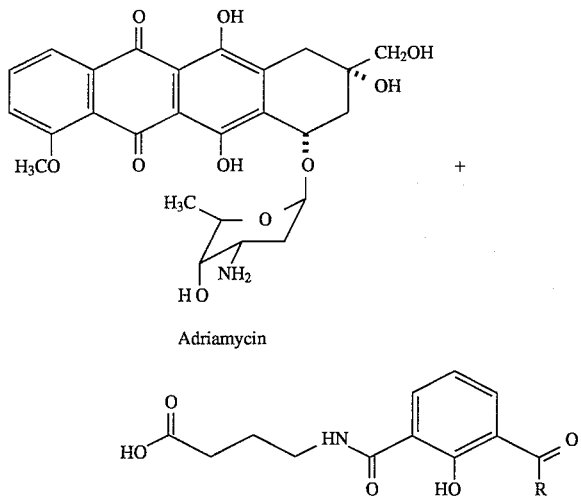

Briefly, formation of a Schiff base linkage is accomplished by briefly refluxing equimolar amounts of adriamycin and substituted aromatic aldehyde linker, or by mixing these reactants in an aprotic solvent in the presence of a dehydrating agent (for instance, a molecular sieve). If tile linker is substituted with a —COOH group, the —COOH is converted to an active ester after formation of the Schiff base-linked adriamycin-linker compound. Alternatively, if the linker is substituted with a maleimide group, no further reaction of the linker prior to reaction with targeting substance is necessary.

The Schiff base-linked adriamycin-linker compound is conjugated with monoclonal antibody (MAb) (i.e., intact MAb, F(ab')$_2$ fragment, F(ab') fragment or Fab fragment). If the targeting substance-reactive group of the adriamycin-linker compound is an active ester, the reaction with MAb will preferably be done at pH 8–10. If the targeting substance reactive group of the adriamycin-linker compound is maleimide, the reaction with MAb will preferably be done at pH 6–7. A range of concentrations of adriamycin-linker compound and MAb is tested in order to determine what concentration of each yields optimal immunoreactivity of the resultant targeting substance conjugate. The optimal concentration of targeting substance reactant required to achieve maximum conjugate immunoreactivity will vary depending on the particular targeting substance to be conjugated (i.e., antibody vs. hormone; one MAb vs. another MAb). The resultant targeting substance-therapeutic agent conjugate may be depicted as follows:

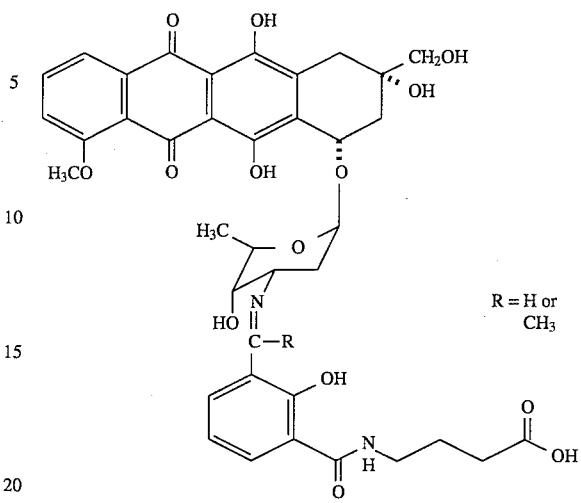

A therapeutically effective amount of the monoclonal antibody-adriamycin Schiff base-linked conjugate is administered intravenously to a tumor-bearing patient. Upon binding of the targeting substance-drug conjugate to an appropriate tumor target cell, thiol groups present at the tumor cell membrane surface may add to the C=N Schiff base imine bond, producing a hemithioaminal (as depicted below). Alternatively, the Schiff base-linked adriamycin-linker compound described above may be conjugated with amine or sulfhydryl groups of a carrier molecule (such as HSA) to produce a slow-release pharmaceutical.

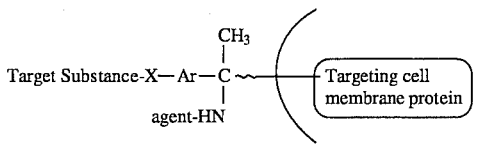

Formation of the hemithioaminal increases retention of the monoclonal antibody-drug conjugate at the tumor cell surface, which in turn may lead to increased tumor cell cytotoxicity.

EXAMPLE V

Stability of Hydrazone Linkers and Corresponding Targeting Substance Conjugates A. Stability of Acetic Hydrazone Derivatives Hydrazone linker serum stability was investigated using corresponding acetic hydrazone derivatives of linker carbonyl compounds.

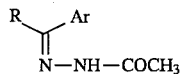

The acetic hydrazone derivatives were incubated at pH 5.6, pH 7.0, and in the presence of human serum at 37° C. Linker stability was evaluated using reverse phase HPLC. Acetic hydrazones of linkers 14, 16 and 17 are stable in serum for greater than 96 hours.

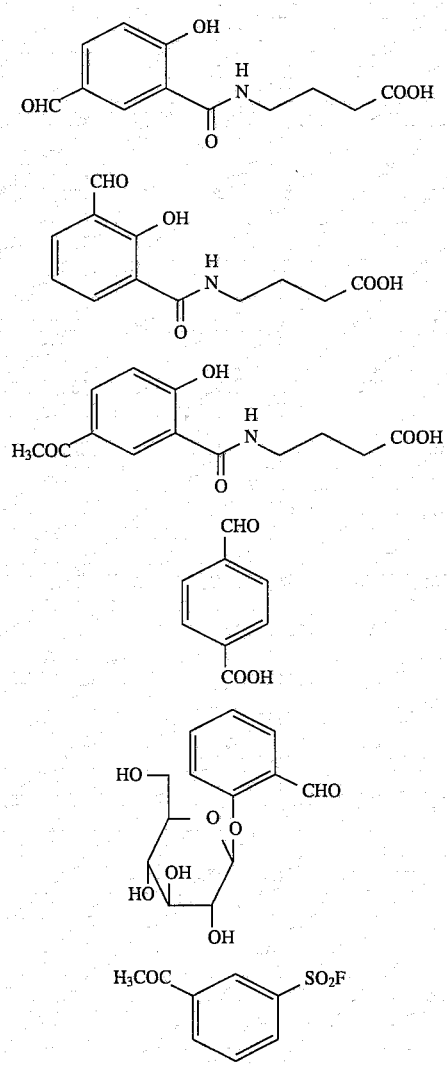

The acetic hydrazone of linker 13 exhibited a linear decomposition over 25 hours to 85% hydrazide and 15% aldehyde, at which point no further degradation took place. The acetic hydrazone of linker 15 demonstrated complete linear degradation to the ketone form over 300 hours, with a $t_{1/2}$ of 130 hours. Thus, linker 15 exhibited sufficient stability to permit tumor localization of a corresponding targeting substance conjugate. The acetic hydrazone of linker 18 (the available sulfonyl fluoride provides linking activity) exhibited a serum stability of $t_{1/2}=7$ days. Based on results obtained with hydrazones of several other linkers at pH 5.6, the acidic pH environment of a tumor target site is predicted to enhance release of linked diagnostic or therapeutic agent in the vicinity of the tumor target.

Acetic hydrazone derivatives of linkers 13, 14 and 15 were tested for stability in acetate buffer at pH 5.6 by HPLC analysis. The derivative of linker 13 degraded to 15–17% aldehyde with no further degradation; the derivative of linker 14 was stable over 96 hours; the derivative of linker 15 displayed linear degradation over 72 hours, with a $t_{1/2}$ of 36 hours. These results indicate that the linkers herein described are stable enough to provide delivery of a linked conjugate to a target site, but labile enough to permit release of a diagnostic or therapeutic agent subsequent to target site localization. Cleavage of the linker may occur by means of target cell mechanisms, such as intracellular pH differences, intracellular enzymes or extracellular membrane nucleophiles.

B. NR-LU-10—5-Acetyl VA Conjugate

NR-LU-10 monoclonal antibody (10 mg) was reacted with an NHS ester of linker 15 [0.961 mg (40 eq.) in 200 μl DMSO made to 2.0 ml with phosphate buffer, pH 7.4] at 4° C. overnight, and the resulting linker-antibody conjugate was purified on a PD-10 column. UV spectral analysis indicated that the conjugate contained 13 molecules of linker per antibody molecule.

VA hydrazide was made by reaction of 185 mg (0.375 mmol) verrucarin A in 1 ml dry chloroform with 45 mg (1.2 eq.) succinic anhydride and a catalytic amount of 4-dimethylaminopyridine (4-DMAP). The reaction mixture was refluxed overnight, cooled and diluted to a volume of 30 ml with dichloromethane. The mixture was washed with 5% HCl, dried over $Na_2SO_4$ and the solvent evaporated. The residue was separated by preparative TLC (Chromatotron: silica, 5% methanol in dichloromethane), yielding 175 mg VA hemisuccinate.

Succinoylsuccinimidate of VA was prepared as follows. N-hydroxysuccinimide (15 mg, 0.1mmol, Aldrich, recrystallized from ethanol) was dissolved in 2 ml dry THF and the solution was cooled in a freezer. Upon cooling, 60 mg (0.1 mmol) VA hemisuccinate and 21 mg dicyclohexyl-carbodiimide were added and the reaction mixture was placed in the freezer for an additional 40 hours. The reaction mixture was filtered, the solvent evaporated, the residue triturated with dichloromethane, and allowed to stand for another 24 hours. The solution was then filtered, the solvent condensed, and the product separated by preparative TLC (Chromatotron: silica, 1% methanol in dichloromethane), yielding 45.9 mg succinoylsuccinimidate of VA.

2'-Hemisuccinoylhydrazide of VA was prepared as follows. Succinoylsuccinimidate of VA (20 mg, 0.0286 mmol) was dissolved in 1 ml THF at room temperature, and 4 ml (0,114 mmol) 95% hydrazine (Aldrich) was added. The reaction was stirred for 1 hour under nitrogen atmosphere and the mixture was filtered. The filtrate was then poured into 5 ml distilled water and extracted with 3×10 ml dichloromethane. A yield of 11 mg of tautomeric 2'-hemisuccinoylhydrazide of VA ("VA hydrazide") was obtained.

VA hydrazide [0.903 mg (100 eq.) VA in 200 μl DMSO made to 2.0 ml with phosphate buffer] was then added to the linker-antibody conjugate (1.94 mg) and reacted for days at 4° C. UV spectral analysis indicated that the MAb-linker-VA conjugate contained 4.4 VA molecules per antibody molecule. Cytotoxicity assays revealed that the MAb-linker-VA conjugate displayed 1 log less cytotoxicity than VA itself.

Alternatively, linker 15-NHS ester may be first reacted with VA hydrazide, then conjugated to antibody, using the same reaction conditions described in the previous paragraph.

C. NR-LU-10—5-Formyl-VA Conjugate

The following conjugate was produced by the same reaction conditions described in Section V.B., above.

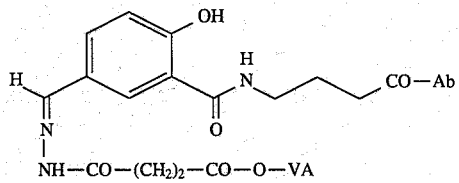

UV calculations indicated a linker/antibody ratio of 10.5:1. VA hydrazide was added to the linker-antibody conjugate and incubated at room temperature overnight with continuous shaking. UV spectral-analysis indicated that the MAb-linker-VA conjugate contained 6.25 VA molecules per antibody molecule. Cytotoxicity assays revealed that the MAb-linker-VA conjugate displayed 1 log less cytotoxicity than VA itself.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method of forming a stabilized Schiff base linkage between a targeting substance and a diagnostic or therapeutic agent, comprising:
   providing a heterobifunctional linker having a maleimide reactive group and a hydrazide reactive group;
   reacting the maleimide reactive group of the heterobifunctional linker with a sulfhydryl reactive site on the targeting substance;
   reacting the hydrazide reactive group of the heterobifunctional linker with an aldehyde or ketone reactive site on the diagnostic or therapeutic reagent to produce a stabilized Schiff base linkage comprising the following structure:

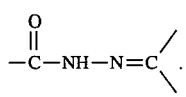

2. The method of claim 1, additionally comprising exposing the targeting substance to a reducing agent to generate a sulfhydryl reactive site from a native targeting substance disulfide bond and reacting the maleimide reactive group of the heterobifunctional linker with the sulfhydryl reactive site on the targeting substance.

3. The method of claim 1, additionally comprising exposing an oligosaccharide of the diagnostic or therapeutic agent to an oxidizing agent to generate an aldehyde or ketone group and reacting the hydrazide reactive group of the heterobifunctional linker with the aldehyde or ketone group on the diagnostic or therapeutic agent.

4. The method of claim 1, wherein the heterobifunctional linker has the following structure:

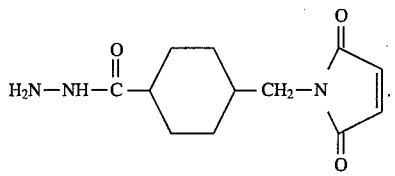

5. A method of forming a stabilized Schiff base linkage between a targeting substance and a diagnostic or therapeutic agent, comprising
   providing a first heterobifunctional linker having a maleimide reactive group and a hydrazide reactive group;
   reacting the maleimide reactive group of the first heterobifunctional linker with a sulfhydryl reactive site on the targeting substance;
   providing a second heterobifunctional linker having a maleimide reactive group and an aldehyde reactive group;
   reacting the maleimide reactive group of the second heterobifunctional linker with a sulfhydryl reactive site on the diagnostic or therapeutic agent to produce an aldehyde reactive site on the diagnostic or therapeutic reagent; and
   reacting the hydrazide reactive group of the first heterobifunctional linker with the aldehyde reactive site on the diagnostic or therapeutic reagent to produce a stabilized Schiff base linkage comprising the following structure:

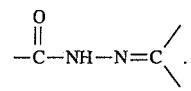

6. The method of claim 5, additionally comprising exposing the diagnostic or therapeutic agent to a reducing agent to generate a sulfhydryl reactive site from a native disulfide bond and reacting the maleimide reactive group of the second heterobifunctional linker with the sulfhydryl reactive site on the diagnostic or therapeutic agent.

7. The method of claim 5, additionally comprising derivatizing the diagnostic or therapeutic agent to introduce a sulfhydryl reactive site and reacting the maleimide reactive group of the second heterobifunctional linker with the sulfhydryl reactive site on the diagnostic or therapeutic agent.

8. The method of claim 5, wherein the second heterobifunctional linker has the following structure:

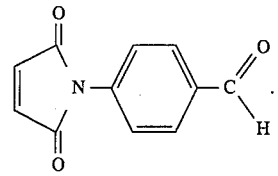

9. A method of forming a stabilized Schiff base linkage between a targeting substance and a diagnostic or therapeutic agent, comprising:
   providing a first heterobifunctional linker having a maleimide reactive group and a hydrazide reactive group;
   reacting the maleimide reactive group of the first heterobifunctional linker with a sulfhydryl reactive site on the targeting substance;
   providing a second heterobifunctional linker having an N-hydroxysuccinimide ester reactive group and an aldehyde reactive group;
   reacting the N-hydroxysuccinimide ester reactive group of the second heterobifunctional linker with a lysine reactive site on the diagnostic or therapeutic agent to produce an aldehyde reactive site on the diagnostic or therapeutic reagent; and
   reacting the hydrazide reactive group of the first heterobifunctional linker with the aldehyde reactive site on the diagnostic or therapeutic reagent to produce a stabilized Schiff base linkage comprising the following structure:

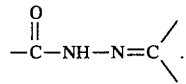

10. The method of claim 9, additionally comprising reacting the N-hydroxysuccinimide ester reactive group of the second heterobifunctional linker with a native lysine residue of the diagnostic or therapeutic agent.

11. The method of claim 9, wherein the second heterobifunctional linker has the following structure:

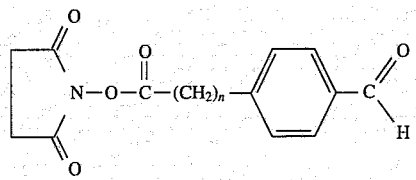

where n=0-6.

12. A method of forming a stabilized Schiff base linkage between a targeting substance and a diagnostic or therapeutic agent, comprising:

providing a first heterobifunctional linker having a maleimide reactive group and a hydrazide reactive group;

reacting the maleimide reactive group of the first heterobifunctional linker with a sulfhydryl reactive site on the diagnostic or therapeutic agent to provide a hydrazide reactive site on the diagnostic or therapeutic agent;

providing a second heterobifunctional linker having a maleimide reactive group and an aldehyde reactive group;

reacting the maleimide reactive group of the second heterobifunctional linker with a sulfhydryl reactive site on the targeting substance to provide an aldehyde reactive site on the targeting substance;

reacting the hydrazide reactive site of the diagnostic or therapeutic agent with the aldehyde reactive site of the targeting substance to produce a stabilized Schiff base linkage comprising the following structure:

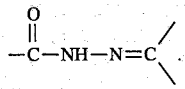

13. The method of claim 12, wherein the first heterobifunctional linker has the following structure:

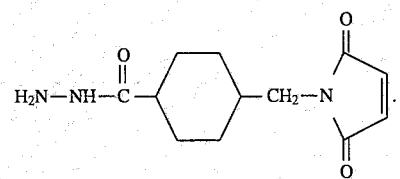

14. The method of claim 12 wherein the second heterobifunctional linker has the following structure:

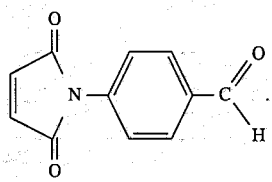

15. The method of claim 12, additionally comprising exposing the diagnostic or therapeutic agent to a reducing agent to generate a sulfhydryl reactive site from a native diagnostic or therapeutic agent disulfide bond and reacting the maleimide reactive group of the first heterobifunctional linker with the sulfhydryl reactive site on the diagnostic or therapeutic agent.

16. The method of claim 12, additionally comprising exposing the targeting substance to a reducing agent to generate a sulfhydryl reactive site from a native disulfide bond on the targeting substance and reacting the maleimide reactive group of the second heterobifunctional linker with the sulfhydryl reactive site on the targeting substance.

17. The method of claim 12, additionally comprising derivatizing the targeting substance to introduce a sulfhydryl reactive site and reacting the maleimide reactive group of the second heterobifunctional linker with the sulfhydryl reactive site on the targeting substance.

* * * * *

UNITED STATES PATENT AND TRADEMARK OFFICE
CERTIFICATE OF CORRECTION

PATENT NO. : 5,521,290

DATED : May 28, 1996

INVENTOR(S) : Sivam et al.

Page 1 of 4

It is certified that error appears in the above-identified patent and that said Letters Patent is hereby corrected as shown below:

| Column | Line | |
|---|---|---|
| [54] (Title) | 2 | "SUBSTANCE-DIAGNOSTIC/THERAPEUTIC" should be SUBSTANCE-DIAGNOSTIC AGENT/THERAPEUTIC-- |
| [75] | 7-10 | "Gowsala P. Sivam, Edmonds; A. Charles Morgan, (Inventors) Jr.; Vivekananda M. Vrudhula, both of Edmonds, all of Wash." should be --Inventors: Gowsala P. Sivam, Edmonds, Washington; Charles Morgan, Jr., Edmonds, Washington; Vivekananda M. Vrudhula, Edmonds, Washington; Michael W. Reed, Seattle, Washington; Anathacari Srinivasan, St. Charles, Missouri; Diana Brixner, Flemington, New Jersery; F. Taha Comezoglu, Kendall Park, New Jersey-- |
| [57] (Abstract) | 49 | "in vivo" should be --*in vivo*-- |

UNITED STATES PATENT AND TRADEMARK OFFICE
CERTIFICATE OF CORRECTION

PATENT NO. : 5,521,290
DATED : May 28, 1996
INVENTOR(S) : Sivam et al.

It is certified that error appears in the above-identified patent and that said Letters Patent is hereby corrected as shown below:

| Column | Line | |
|---|---|---|
| 3 | 32-35 | The formula reading 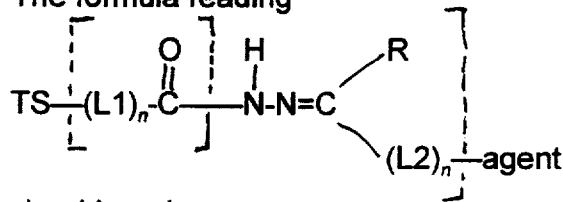 should read 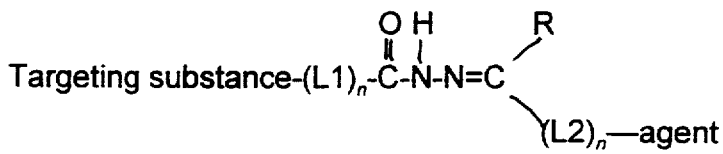 OR 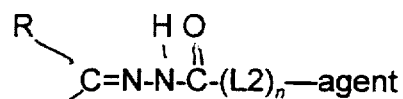 |
| 3 | 51 | "The bracketed portion of the" should be --The-- |
| 3 | 52 | "represents the" should be --includes a-- |
| 4 | 31 | "Pseudomonas" should be --<u>Pseudomonas</u>-- |

UNITED STATES PATENT AND TRADEMARK OFFICE

CERTIFICATE OF CORRECTION

PATENT NO.    : 5,521,290

DATED         : May 28, 1996

INVENTOR(S)   : Sivam et al.

It is certified that error appears in the above-identified patent and that said Letters Patent is hereby corrected as shown below:

| Column | Line | |
|---|---|---|
| 4 | 32 | "Diptheria" should be --Diptheria-- |
| 4 | 35 | "Pseudomonas" should be --Pseudomonas-- |
| 4 | 35 | "Diptheria" should be --Diptheria-- |
| 9 | 67 | "herein.  A" should be --herein.[paragraph break][indent]A-- |
| 13 | 5 | "$^{90m}$Tc" should be --$^{99m}$Tc-- |
| 13 | 10 | "ligand-plus" should be --ligand plus-- |
| 14 | 11 | "by substituents" should be --by Ar substituents-- |
| 18 | 45 | "Of" should be --of-- |
| 19 | 66 | "SnSu$_3$" should be --SnBu$_3$-- |
| 20 | 42 | "Danvets" should be --Danvers-- |

UNITED STATES PATENT AND TRADEMARK OFFICE

CERTIFICATE OF CORRECTION

PATENT NO. : 5,521,290

DATED : May 28, 1996

INVENTOR(S) : Sivam et al.

It is certified that error appears in the above-identified patent and that said Letters Patent is hereby corrected as shown below:

| Column | Line | |
|---|---|---|
| 21 | 44 | "tile" should be --the-- |
| 24 | 5 | "C." should be --C-- |
| 24 | 36 | "0,114" should be --0.114-- |

Signed and Sealed this

First Day of April, 1997

Attest:

BRUCE LEHMAN

Attesting Officer

Commissioner of Patents and Trademarks